United States Patent
Secrist et al.

(10) Patent No.: US 12,247,142 B2
(45) Date of Patent: Mar. 11, 2025

(54) TACKIFIER-FREE HOT MELT ADHESIVE COMPOSITIONS SUITABLE FOR USE IN A DISPOSABLE HYGIENE ARTICLE

(71) Applicants: Bostik, Inc., Wauwatosa, WI (US); Bostik, SA, Colombes (FR)

(72) Inventors: Kimberly E. Secrist, Wauwatosa, WI (US); Steven D. Gray, Wauwatosa, WI (US); Naji Hussein, Colombes (FR)

(73) Assignees: Bostik Inc., Wauwatosa, WI (US); Bostik SA, Colombes (FR)

( * ) Notice: Subject to any disclaimer, the term of this patent is extended or adjusted under 35 U.S.C. 154(b) by 340 days.

(21) Appl. No.: 17/626,238

(22) PCT Filed: Jul. 10, 2020

(86) PCT No.: PCT/US2020/041640
§ 371 (c)(1),
(2) Date: Jan. 11, 2022

(87) PCT Pub. No.: WO2021/011390
PCT Pub. Date: Jan. 21, 2021

(65) Prior Publication Data
US 2022/0251429 A1 Aug. 11, 2022

Related U.S. Application Data

(60) Provisional application No. 62/873,259, filed on Jul. 12, 2019.

(51) Int. Cl.
B32B 41/00 (2006.01)
A61F 13/539 (2006.01)
C09J 5/06 (2006.01)
C09J 123/12 (2006.01)

(52) U.S. Cl.
CPC .......... *C09J 123/12* (2013.01); *A61F 13/539* (2013.01); *C09J 5/06* (2013.01); *A61F 2013/53958* (2013.01)

(58) Field of Classification Search
CPC .......... C09J 123/12; C09J 5/06; A61F 13/539; A61F 2013/53958; A61F 2013/5395; C08L 23/20; C08L 23/02
USPC .................. 156/60, 64, 350, 351, 378, 379
See application file for complete search history.

(56) References Cited

U.S. PATENT DOCUMENTS

| | | |
|---|---|---|
| 6,797,774 B2 | 9/2004 | Kijima |
| 7,776,242 B2 | 8/2010 | Sato et al. |
| 8,282,731 B2 | 10/2012 | Bruce et al. |
| 8,623,480 B2 | 1/2014 | Davis |
| 9,139,755 B2 | 9/2015 | Bunnelle |
| 9,241,843 B2 | 1/2016 | Bunnelle et al. |
| 9,695,340 B2 | 7/2017 | Moriguchi et al. |
| 9,822,283 B2 | 11/2017 | Inoue |
| 10,011,744 B2 | 7/2018 | Wang et al. |
| 11,149,170 B2 | 10/2021 | Matsuda |
| 11,877,913 B2 | 1/2024 | Bunnelle et al. |
| 2008/0213515 A1 | 9/2008 | Vey et al. |
| 2014/0079919 A1 | 3/2014 | Bunnelle |
| 2014/0147699 A1 † | 5/2014 | Thatcher |
| 2014/0199545 A1 † | 7/2014 | Moriguchi |
| 2016/0102230 A1 † | 4/2016 | Gray |
| 2016/0270987 A1 | 9/2016 | Stiehl et al. |
| 2016/0289511 A1 | 10/2016 | Sustic et al. |
| 2017/0114257 A1 | 4/2017 | Hussein et al. |
| 2017/0165125 A1 | 6/2017 | Turner |
| 2017/0165130 A1 | 6/2017 | Turner |
| 2017/0165133 A1 | 6/2017 | Turner |
| 2017/0165396 A1 | 6/2017 | Turner |
| 2017/0204306 A1 † | 7/2017 | Wang |
| 2017/0209616 A1 | 7/2017 | Turner |
| 2017/0240784 A1 † | 8/2017 | Jin |
| 2017/0260430 A1 † | 9/2017 | Moriguchi |
| 2018/0029344 A1 † | 2/2018 | Hamm |
| 2018/0030317 A1 † | 2/2018 | Fujinami |
| 2018/0148616 A1 † | 5/2018 | Okazaki |
| 2020/0010742 A1 † | 1/2020 | Corzani |
| 2020/0108167 A1 | 4/2020 | Turner et al. |

FOREIGN PATENT DOCUMENTS

| | | |
|---|---|---|
| JP | H01282280 A | 11/1989 |
| JP | 2017538806 A1 † | 12/2017 |
| JP | 2019077834 A2 | 5/2019 |
| WO | 2013039261 A1 † | 3/2013 |
| WO | WO2013060732 A1 | 5/2013 |
| WO | WO2015095480 A1 | 6/2015 |
| WO | WO2016207444 A1 | 12/2016 |
| WO | WO17047805 A1 | 3/2017 |
| WO | WO2018007451 A1 | 1/2018 |
| WO | 201903964 A1 † | 1/2019 |

† cited by third party

*Primary Examiner* — Michael N Orlando
*Assistant Examiner* — Joshel Rivera
(74) *Attorney, Agent, or Firm* — Christopher R. Lewis

(57) ABSTRACT

A hot melt adhesive composition comprises a polypropylene homopolymer having a DSC melting point of less than 100° C.; a butene-based copolymer; and a plasticizer. The butene-based copolymer may comprise a butene-rich amorphous poly-alpha olefin, such as a butene-propylene copolymer, or a semi-crystalline copolymer, such as a butene-ethylene copolymer. The hot melt adhesive is especially useful for bonding substrates which swell or elongate significantly in use. Such uses include adhering superabsorbent polymers to a substrate or adhering together two substrates at least one of which having superabsorbent polymers, such as the top and bottom layer of an absorbent core of a disposable hygiene article, such as a diaper, feminine sanitary napkin, and adult incontinence pad. The hot melt adhesive composition, which does not contain a tackifier, demonstrates suitable elongation at break and stress at yield, with a sufficiently low viscosity, to stabilize an absorbent core having superabsorbent polymers.

21 Claims, No Drawings

TACKIFIER-FREE HOT MELT ADHESIVE COMPOSITIONS SUITABLE FOR USE IN A DISPOSABLE HYGIENE ARTICLE

CROSS-REFERENCE TO RELATED APPLICATIONS

This patent application is a U.S. national stage application under 35 U.S.C. § 371 of international application number PCT/US2020/041640, filed Jul. 10, 2020, which claims the benefit under 35 U.S.C. § 119 (e) of U.S. patent application Ser. No. 62/873,259, filed on Jul. 12, 2019.

FIELD OF THE INVENTION

This invention relates to tackifier-free hot melt adhesive compositions suitable for use in a disposable hygiene article, such as a diaper and training pants. The adhesive is especially well-suited for applications that require a high elongation at break and stress at yield, without having too high of a viscosity at the desired application temperature.

BACKGROUND OF THE INVENTION

Hot melt adhesives typically exist as a solid mass at ambient temperature and can be converted to a flowable liquid by the application of heat. These adhesives are particularly useful in manufacturing a variety of disposable goods where bonding of various substrates is often necessary. Specific applications include disposable diapers, hospital pads, feminine sanitary napkins, panty shields, surgical drapes and adult incontinent briefs, collectively known as disposable nonwoven hygienic products. Other diversified applications have involved paper products, packaging materials, automotive headliners, appliances, tapes and labels. In most of these applications, the hot melt adhesive is heated to its molten state and then applied to a substrate, often named as the primary substrate. A second substrate, often named as the secondary substrate, is then immediately brought into contact with and compressed against the first. The adhesive solidifies on cooling to form a strong bond. The major advantage of hot melt adhesives is the absence of a liquid carrier, as would be the case of water or solvent based adhesives, thereby eliminating the costly process associated with solvent removal.

For many applications, hot melt adhesives are often extruded directly onto a substrate in the form of a thin film or a bead by using piston or gear pump equipment. In this case, the substrate is brought into intimate contact with a hot die under pressure. The temperature of the die must be maintained well above the melting point of the adhesive to allow the molten hot melt material to flow through the application nozzle smoothly. For most applications, particularly those encountered in food packaging and disposable nonwovens hygienic article manufacturing, bonding of delicate and heat sensitive substrates, such as thin gauge plastic films, is often involved. This imposes an upper limit on coating temperature for hot melt adhesive applications. Today's commercial hot melts are typically formulated to have coating temperature below 200° C. to avoid substrate burning or distortion. Besides directly coating, several indirect or noncontact coating methods, through which a hot melt adhesive can be spray-coated with the aid of compressed air onto a substrate from a distance, have also been developed. These non-contact coating techniques include conventional spiral spray, Signature™, Control Coat™, UFD™, and various forms of melt-blown methods. The indirect method, however, requires that the viscosity of the adhesives must be sufficiently low, usually in the range of 2,000 to 30,000 mPa·s, often in the range of 2,000 to 15,000 mPa·s, at the application temperature in order to obtain an acceptable coating pattern.

Hot melt adhesives are traditionally comprised of polymers, plasticizers, tackifying resins (also referred to herein as "tackifiers"), and optionally additives such as waxes and anti-oxidants. Tackifiers have long been considered a necessary component of hot melt adhesives. Traditionally, the role of tackifiers with styrene-block-copolymer systems is to increase tack by increasing the glass transition temperature of the adhesive system. Tackifiers additionally help suppress the viscosity of the final formulation. However, tackifiers can be viewed negatively because they can contribute odor and volatile organic compounds (VOCs) to the adhesive formulation.

Efforts have been made to develop tackifier-free hot melt adhesives. For example, U.S. Pat. No. 9,139,755 discloses a hot melt adhesive composition comprising about 90 to 10 wt. % of an amorphous polyolefin copolymer composition comprising 50 to 70 wt. % 1-butene; about 10 to 90 wt. % of a heterophase polypropylene copolymer composition comprising propene and a comonomer comprising ethylene, 1-hexene or 1-octene and comprising amorphous character and crystalline blocks; and about 0.1 to 30 wt. % of a polyisobutylene plasticizer made with an $AlCl_3$; wherein the adhesive provides cohesive strength from the heterophase polypropylene copolymer and adhesive strength from the amorphous polyolefin copolymer.

In addition, U.S. Pat. No. 8,623,480 discloses a hot melt adhesive composition comprising at least 55% by weight of a first polymer consisting of a non-functionalized amorphous poly alpha olefin polymer comprising greater than about 50% by weight polypropylene; a second polymer selected from the group consisting of polypropylene homopolymers, propylene copolymers, and combinations thereof; a functionalized polypropylene wax; and polyethylene wax, which is preferably tackifier-free.

International Patent Application No. WO 2013/039261 discloses a hot melt adhesive including: (A) a propylene homopolymer having a melting point of 100° C. or lower which is obtainable by polymerizing propylene using a metallocene catalyst; and (B) an ethylene-based copolymer.

SUMMARY OF THE INVENTION

There still exists a need in the art for an adhesive which has low tack and a sufficiently high elongation at break and high stress at yield to be able to withstand the swelling of a superabsorbent polymer when wet, yet still has a suitable viscosity at the desired application temperature.

Therefore, it would be advantageous to provide a hot melt adhesive that will overcome the shortcomings of the prior art adhesives mentioned above. In particular, it is desired to make a hot melt adhesive which does not contain any tackifiers. Such an adhesive is desirably polyolefin-based because such adhesives can handle high temperatures well and are generally perceived as having lower odor. Such an adhesive would have a sufficiently high elongation at break and high stress at yield to be able to withstand the swelling of a superabsorbent polymer when wet, yet still has a suitable viscosity at the desired application temperature. Such an adhesive would be particularly well suited as a micro-fiberized adhesive, responsible for containing superabsorbent polymers (SAP) within a hygiene article, such as a diaper, either alone or in conjunction with another adhesive and/or cellulose fibers. The adhesive would not be required to have a high degree of tack, but is required to have very good elongation to contain the SAP as it swells/expands. A challenge in making a tackifier-free adhesive is developing a formulation low enough in viscosity to process, but "strong" enough to meet mechanical properties, such as elongation at break.

In view of the shortcomings of the prior art, the present invention provides a hot melt adhesive composition comprising a polypropylene homopolymer having a DSC melting point of less than 100° C.; a 1-butene-based copolymer; and a plasticizer, wherein the adhesive is tackifier-free. Such a composition provides both high elongation at break and stress at yield, although having a sufficiently low viscosity to be able to be processed.

In accordance with an embodiment of the present invention, a method of making a laminate comprises the steps of: applying the hot melt adhesive composition of the invention in a molten state to a primary substrate; and mating a secondary substrate to the first substrate by contacting the secondary substrate with the adhesive composition.

In accordance with another embodiment of the present invention, an absorbent core comprises a first layer and a second layer, wherein at least one of the first layer and the second layer comprises superabsorbent polymers, and the first layer and the second layer are adhered to each other by a hot melt adhesive composition of the present invention and the adhesive composition adheres the superabsorbent polymers within the absorbent core.

In accordance with another embodiment of the present invention, a disposable hygiene article comprises the absorbent core of the invention.

DETAILED DESCRIPTION OF THE INVENTION

In accordance with the present invention, a hot melt adhesive composition comprises a polypropylene homopolymer having a DSC melting point of less than 100° C.; a 1-butene-based copolymer; and a plasticizer, wherein the adhesive is tackifier-free. Such a composition provides both high elongation at break and stress at yield, although having a sufficiently low viscosity to be able to be processed. Such an adhesive is particularly well-suited to applications requiring the ability to elongate in use to a great extent (e.g., such as by 400%) and offer a high stress at yield (such as at least 0.5 MPa), despite having a relatively low viscosity such as equal to or less than about 30,000 centipoise (cP) at 163° C. (325° F.) and equal to or less than about 17,500 centipoise (cP) at 177° C. (350° F.).

The polypropylene homopolymer used in the invention has a DSC melting point of less than 100° C., more preferably between 60° C. and 90° C. As used herein, a "DSC melting point" refers to a melting point measured using Differential Scanning Calorimetry (DSC) according to ASTM E-794-01. The weight average molecular weight of the polypropylene homopolymer is preferably between about 5,000 and about 150,000 daltons, preferably between about 30,000 and about 90,000 daltons, and most preferably between about 35,000 and about 85,000 daltons. As used herein, when referring to the weight average molecular weight of any constituent herein, the weight average molecular weight is determined by gel permeation chromatography using polypropylene standards.

An exemplary type of polypropylene homopolymer has been developed by Idemitsu Petrochemical, Ltd. This type of polymer has been described as their L-MODU grades, which is short for low molecular weight and low modulus polyolefin. Although they are entirely polypropylene based, they have properties not normally associated with polypropylene. Conventional polypropylene homopolymers tend to be very high in crystallinity and melting point. This is true whether or not they were prepared using Zeigler-Natta or metallocene catalysts technology. The L-MODU grades are made using a metallocene catalyst which controls the stereoregularity of the polymer. This results in a polymer which gives properties that were not attainable before. For example, the melting points of these new polymers are much lower than any other metallocene catalyzed polypropylene homopolymer. Typical polypropylene homopolymers have Melt Peaks of about 130° C. to 170° C. when measured by Differential Scanning Calorimetry as in ASTM E794-01. The L-MODU polymers have Ring and Ball Softening points of under 130° C. when measured according to ASTM E-28-99. When measured using Differential Scanning Calorimetry (DSC) according to ASTM E-794-01, they have melting points less than 100° C. and more preferably between 60° C. and 90° C.

The process to make these polymers is described in detail in U.S. Pat. No. 6,797,774 (assigned to Idemitsu Petrochemical Co., Ltd. of Tokyo, Japan) along with various hot melt adhesive formulations. Because they have such low melting points and long recrystallization times, special considerations need to be taken into account to process them using underwater pelletizing equipment. This is described in U.S. Pat. No. 7,776,242, assigned to Idemitsu Kosan Co., Ltd. of Tokyo, JP. The disclosures found in U.S. Pat. Nos. 6,797,774 and 7,776,242 are both specifically incorporated herein by reference thereto.

Even though the L-MODU polymers are polypropylene homopolymers, they are very different from traditional polypropylene polymers, as mentioned previously. Besides having much lower melting points when measured by DSC, their Melt Enthalpy values are also much lower than traditional polypropylene grades. When analyzed according to ASTM E793-01 "Standard Test Method for Enthalpies of Fusion and Crystallization by Differential Scanning Calorimetry", the following results in Table 1 are obtained. The test was modified slightly to use a scanning temperature of 20° C. per minute instead of 10° C. per minute.

TABLE 1

| L-MODU grade | Glass Transition Temperature (Tg) | Melt Peak | Melt Enthalpy |
|---|---|---|---|
| S-400 | −9.7° C. | 77.6° C. | 4.9 Joules/gram |
| S-600 | −7.8° C. | 77.1° C. | 22.6 Joules/gram |
| S-900 | −8.0° C. | 76.9° C. | 22.6 Joules/gram |

Both the Melt Peak and Melt Enthalpy values are very low compared to most traditional polypropylene based homopolymers. Typical polypropylene homopolymers have melting points of from about 130° C. to 171° C. and melt enthalpy values of about 80 J/g or higher. The L-MODU polymers have a unique combination of melting point and melt enthalpy. However, to make a suitable hot melt adhesive for the desired application using these materials as a base polymer requires the use of an additional polymer, namely a 1-butene-based copolymer.

The hot melt adhesive composition of the present invention further comprises a 1-butene-based copolymer. As used herein, the term "butene-based" copolymer means that the copolymer comprises greater than 50 mol % butene and is made of at least one other monomer in addition to butene. In an embodiment of the invention, the 1-butene-based copolymer comprises a butene-rich amorphous poly-alpha olefin. As used herein, the term "butene-rich" copolymer means that the copolymer comprises greater than 50 mol % butene. As used herein, an amorphous poly-alpha olefin (APAO) refers to a class of low molecular weight amorphous propylene copolymers with butene and at least one other monomer typically produced with a Lewis acid catalyst. Preferably, the 1-butene-rich amorphous poly-alpha olefin comprises a butene-propylene copolymer. In another embodiment, the 1-butene-based copolymer comprises a semi-crystalline copolymer. Preferably, the semi-crystalline copolymer comprises a butene-ethylene copolymer. In still another embodiment, the 1-butene-based copolymer comprises a blend of a butene-rich amorphous poly-alpha olefin and a semi-crystalline copolymer.

In general, the weight average molecular weight of the 1-butene-based copolymer is preferably between about 15,000 and about 160,000 daltons, preferably between about 40,000 and about 150,000 daltons, and most preferably between about 45,000 and about 145,000 daltons. In embodiments in which the 1-butene-based copolymer comprises a butene-rich amorphous poly-alpha olefin, the weight average molecular weight of the butene-rich amorphous poly-alpha olefin is between about 15,000 and about 85,000 daltons, preferably between about 40,000 and about 65,000 daltons, and most preferably between about 45,000 and about 60,000 daltons.

The hot melt adhesive composition of the present invention further comprises a plasticizer. The plasticizer may be any known compatible plasticizer and preferably is selected from the group consisting of mineral oil, synthetic poly-alphaolefin oils, and polyisobutylene. A suitable plasticizer may also be selected from olefin oligomers and low molecular weight polymers, as well as vegetable and animal oils and derivatives thereof. The petroleum derived oils which may be employed are relatively high boiling materials containing only a minor proportion of aromatic hydrocarbons. In this regard, the aromatic hydrocarbons should preferably be less than 30% and more particularly less than 15% of the oil, as measured by the fraction of aromatic carbon atoms. More preferably, the oil may be essentially non-aromatic. The oligomers may be polypropylenes, polybutenes, hydrogenated polyisoprenes, hydrogenated polybutadiens, or the like having average molecular weight between about 350 g/mole and about 10,000 g/mole. Suitable vegetable and animal oils include glycerol esters of the usual fatty acids and polymerization products thereof.

Other useful plasticizers can be found in the families of conventional dibenzoate, phosphate, phthalate esters, as well as esters of mono- or polyglycols. Examples of such plasticizers includes, but are not limited to dipropylene glycol dibenzoate, pentaerythritol tetrabenzoate, 2-ethylhexyl diphenyl phosphate, polyethylene glycol 400-di-2-ethylhexoate; butyl benzyl phthalate, dibutyl phthalate and dioctylphthalate. The plasticizers that find usefulness in the present invention can be any number of different plasticizers but the inventors have discovered that mineral oil and liquid polybutenes having average molecular weight less than 5,000 daltons are particularly advantageous. As will be appreciated, plasticizers have typically been used to lower the viscosity of the overall adhesive composition without substantially decreasing the adhesive strength and/or the service temperature of the adhesive as well as to extend the open time and to improve flexibility of the adhesive.

According to embodiments of the invention, the polypropylene homopolymer is present in an amount of between about 20% and about 75% by weight, preferably between about 25% and about 65% by weight, and most preferably between about 30% and about 60% by weight, based on the total weight of the composition; the 1-butene-based copolymer is present in an amount of between about 3% and about 50% by weight, preferably between about 4% and about 45% by weight, and most preferably between about 5% and about 35% by weight, based on the total weight of the composition; and the plasticizer is present in an amount of between about 20% and about 60% by weight, preferably between about 25% and about 55% by weight, and most preferably between about 30% and about 40% by weight, based on the total weight of the composition.

According to embodiments of the invention, the weighted average of the weight average molecular weights of the polypropylene homopolymer and the butene-based copolymer is between about 60,000 and about 80,000 daltons, preferably between about 64,000 and about 76,000 daltons, and most preferably between about 66,000 and about 74,000 daltons. The weighted average of the weight average molecular weights of the polymers is determined by adding the products of the weight fraction of each polymer (based on the total weight of the polymers) and its weight average molecular weight.

The present invention may optionally include an antioxidant, also referred to as a stabilizer. If included, the antioxidant may be present in an amount of from about 0.1% to about 3% by weight of the total adhesive composition. Preferably, from about 0.2% to 2% of an antioxidant is incorporated into the composition. The antioxidants which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Among the applicable antioxidants are high molecular weight hindered phenols and multifunction phenols, such as sulfur and phosphorous-containing phenols. Hindered phenols are well known to those skilled in the art and may be characterized as phenolic compounds that also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include: 1,3,5-trimethyl-2,4,6-tris(3-5-di-tert-butyl-4-hydroxybenzyl) benzene; pentaerythirtol tetrakis-3(3,5-di-tert-butyl-4-hydroxyphenyl) propionate; n-octadecyl-3(3,5-di-tert-butyl-4-hydroxyphenyl) propionate; 4,4'-methylenebis(4-methyl-6-tert butylphenol); 2,6-di-tert-butylphenol; 6-(4-hydroxyphenoxy)-2,4-bis(n-octylthio)-1,3,5-triazine; 2,3,6-tris(4-hydroxy-3,5-di-tert-butyl-phenoxy)-1,3,5-triazine; di-n-octadecyl-3,5-di-tert-butyl-4-hydroxybenzylphosphonate; 2-(n-octylthio)ethyl-3,5-di-tert-butyl-4-hydroxybenzoate; and sorbitol hexa-3(3,5-di-tert-butyl-4-hydroxy-phenyl) propionate.

The performance of these antioxidants may be further enhanced by utilizing, in conjunction therewith; (1) synergists such as, for example, thiodipropionate esters and phosphites; and (2) chelating agents and metal deactivators as, for example, ethylenediaminetetraacitic acid, slats thereof, and disalicylalpropylenediimine.

It should be understood that other optional additives may be incorporated into the adhesive composition of the present invention in order to modify particular physical properties. These may include, for example, such materials as inert colorants e.g. titanium dioxide, fillers, fluorescent agents, UV absorbers, surfactants, other types of polymers, etc. Typical fillers include talc, calcium carbonate, clay silica, mica, wollastonite, feldspar, aluminum silicate, alumina, hydrated alumina, glass microspheres, ceramic microspheres, thermoplastic microspheres, baryte and wood flour. Surfactants are particularly important in hygienic disposable nonwoven because they can dramatically reduce the surface tension, for example, of the adhesive applied to diaper core, thereby permitting quicker transport and subsequent absorption of urine by the core.

According to embodiments of the invention, waxes are included in the adhesive composition. Such waxes could include low molecular weight waxes, petroleum waxes such as paraffin wax, synthetic waxes, and polyolefin waxes. Preferably, the adhesive composition contains substantially no wax, such as less than 1% by weight, more preferably less than 0.5% by weight based on the total weight of the composition, and most preferably no wax.

According to embodiments of the invention, a hot melt adhesive composition consists essentially of a polypropylene homopolymer having a DSC melting point of less than 100° C.; a 1-butene-based copolymer; and a plasticizer, whereby the composition is tackifier-free. According to further embodiments of the invention, a hot melt adhesive composition consists of a polypropylene homopolymer having a DSC melting point of less than 100° C.; a 1-butene-based copolymer; and a plasticizer, whereby the composition is tackifier-free. By being tackifier-free, the composition contains no tackifiers or only de minimus amounts of tackifiers known in the art for use in hot melt adhesives, such as those are disclosed in U.S. Pat. No. 10,011,744, incorporated herein by reference. Classes of such tackifiers include: aliphatic and cycloaliphatic petroleum hydrocarbon resins; aromatic petroleum hydrocarbon resins and hydrogenated derivatives thereof; aliphatic/aromatic petroleum derived hydrocarbon resins and the hydrogenated derivatives thereof; aromatic modified cycloaliphatic resins and the hydrogenated derivatives thereof; polyterpene resins having a softening point of from about 10° C. to about 140° C.; copolymers and terpolymers of natural terpenes; natural and modified rosin; glycerol and pentaerythritol esters of natural and modified rosin; and phenolic-modified terpene resins.

The hot melt composition of the present invention is further characterized by having a low viscosity as measured per ASTM-D3236 with Spindle 27 by using a Brookfield viscometer at 163° C. (325° F.) and at 177° C. (350° F.). The spindle speed was adjusted so the percent torque was about 45-90%. The viscosity of the composition is preferably equal to or less than about 30,000 centipoise (cP) at 163° C. (325° F.), more preferably equal to or less than about 22,500 centipoise (cP) at 163° C. (325° F.), and most preferably equal to or less than about 15,000 centipoise (cP) at 163° C. (325° F.). The viscosity of the composition is preferably equal to or less than about 17,500 centipoise (cP) at 177° C. (350° F.), preferably equal to or less than about 15,000 centipoise (cP) at 177° C. (350° F.), and most preferably equal to or less than about 12,500 centipoise (cP) at 177° C. (350° F.). In embodiments of the invention, the heat of fusion of the composition obtained by DSC according to ASTM E793-01 is less than 40 J/g, preferably less than about 35 J/g, more preferably less than about 25 J/g, still more preferably less than about 20 J/g, and most preferably less than about 15 J/g. In embodiments of the invention, the composition has a stress at yield of at least about 0.5 MPa, preferably at least about 0.7 MPa, and most preferably at least about 0.9 MPa. Stress at yield is determined by mechanical properties as determined by an Instron. In embodiments of the invention, the composition has an elongation at break of at least about 350%, preferably at least about 375%, more preferably at least about 390%, and most preferably at least about 400%. Elongation at break is determined by the Elongation test set forth in the Examples below.

It has been found that this combination of properties provides an adhesive which is particularly suitable for use to stabilize an absorbent core having super-absorbent polymers. Included within this invention is any combination of the above range limits of viscosity, stress at yield, and elongation at break. For example, in one embodiment of the invention, the adhesive has viscosities equal to or less than about 22,500 centipoise (cP) at 163° C. (325° F.) and equal to or less than about 15,000 centipoise (cP) at 177° C. (350° F.), has a stress at yield of at least about 0.9 MPa, and has an elongation at break of at least about 390%.

The hot melt adhesive composition of the present invention may be formulated by using any of the mixing techniques known in the art. A representative example of the mixing procedure involves placing all the components in a jacketed mixing kettle equipped with a rotor, and thereafter raising the temperature of the mixture to a range from 150° C. to 200° C. to melt the contents. Any of the constituents may be pre-blended or added individually to the mixing kettle. For example, the polymers can be a preformed mixture or blend or can be added to the mixing kettle individually. It should be understood that the precise temperature to be used in this step would depend on the melting points of the particular ingredients. The mixing is allowed to continue until a consistent and uniform mixture is formed. The content of the kettle is protected with inert gas such as carbon dioxide or nitrogen during the entire mixing process. Without violating the spirit of the present invention, various additions and variation can be made to the present invention procedure to produce the hot melt composition, such as, for example, applying vacuum to facilitate the removal of entrapped air. Other equipment useful for formulating the composition of the present invention includes, but not limited to, single or twin screw extruders or other variations of extrusion machinery, kneaders, intensive mixers, Ross™ mixers, and the like. The hot melt adhesive is then cooled to room temperature and formed into chubs with a protective skin formed thereon or into pellets for shipment and use.

The adhesive composition of the present invention may be used as a general purpose hot melt adhesive in a number of applications such as, for example, in disposable nonwoven hygienic articles, paper converting, flexible packaging, wood working, carton and case sealing, labeling and other assembly applications. Particularly preferred applications include nonwoven disposable diaper and feminine sanitary napkin construction, diaper and adult incontinent brief elastic attachment, diaper and napkin core stabilization, diaper backsheet lamination, industrial filter material conversion, surgical gown and surgical drape assembly, etc.

The resulting hot melt adhesives may be applied to substrates using a variety application techniques. Examples includes hot melt glue gun, hot melt slot-die coating, hot melt wheel coating, hot melt roller coating, melt blown coating, spiral spray, contact or noncontact strand coatings branded as Signature™, Control Coat™, UFD™, and the like. In a preferred embodiment, the hot melt adhesive is directly applied onto the substrates.

In an embodiment of the invention, a method of making a laminate comprises the steps of: (1) applying the hot melt adhesive composition of the invention in a molten state to a primary substrate; and (2) mating a secondary substrate to the first substrate by contacting the secondary substrate with the adhesive composition. In an embodiment of the invention, the first substrate comprises a first layer (such as a bottom layer) of an absorbent core and the secondary substrate comprises a second layer (such as a top layer) of the absorbent core, wherein at least one of the first layer or the second layer have superabsorbent polymers associated therewith. The first substrate and secondary substrate may be a single continuous material, but folded over, so that the two folds form the first and secondary substrate.

Any suitable absorbent core having superabsorbent polymers may be used in connection with the present invention. Suitable absorbent cores are described in U.S. Patent Application Nos. 2017/0209616; 2017/0165133; and 2016/0270987, all of which are incorporated herein by reference. As described in U.S. Patent Application No. 2017/0165133, the absorbent core structure typically includes absorbent polymer material, such as hydrogel-forming polymer material, also referred to as absorbent gelling material, AGM, or super-absorbent polymer, SAP. This absorbent polymer material ensures that large amounts of bodily fluids, e.g. urine, can be absorbed by the absorbent article during its use and be locked away, thus providing low rewet and good skin dryness. Thinner absorbent core structures can be made by reducing or eliminating the traditional use of cellulose or cellulosic fibers in the absorbent core structure. To maintain the mechanical stability of these absorbent core structures, a fiberized net structure, which in some cases may be an adhesive, may be added to stabilize the absorbent polymer material. The absorbent core may also have additional adhesives, either to assist the fiberized net structure adhesive and/or to bond other core materials to each other and/or to other article components. The superabsorbent polymer material may be deposited on or associated with the first and second substrates and a fiberized net structure covers the superabsorbent polymer material on the respective first and second substrates.

In embodiments of the invention, the fiberized net structure comprises an adhesive composition of the present invention. The fiberized net structure may contain other materials, such as other adhesives or cellulose fibers. In another embodiment of the invention, the sole adhesive used in the fiberized net structure is an adhesive composition of the present invention. In still other embodiments of the invention, the fiberized net structure consists solely of one or more adhesive compositions of the present invention. In an embodiment of the invention, the first and second absorbent layers are combined together such that at least a portion of the fiberized net structure of the first absorbent layer contacts at least a portion of the fiberized net structure of the second absorbent layer and wherein an adhesive of the present invention used in the fiberized net structure serves to adhere to two layers together to form the absorbent core. In embodiments of the invention, both the first and second layers of the absorbent core have superabsorbent polymers associated therewith. In other embodiments of the invention, only one of the layers has superabsorbent polymers associated therewith.

In another embodiment of the method of making a laminate of the invention, the primary substrate is a first layer of an absorbent core and the secondary substrate is a superabsorbent polymer. The super-absorbent polymer may be deposited on the first layer before the application of the adhesive composition. In this embodiment, the adhesive may form a fiberized net over and around the superabsorbent polymer and may also adhere to the first layer. In a further embodiment, a second layer is formed in the same way and then the two layers are mated, before the adhesive is cooled, to form an absorbent core.

ASPECTS OF THE INVENTION

1. A hot melt adhesive composition comprising:
   a polypropylene homopolymer having a DSC melting point of less than 100° C.;
   a 1-butene-based copolymer; and
   a plasticizer;
   wherein the composition is tackifier-free.

2. The composition of aspect 1, wherein the 1-butene-based copolymer comprises a butene-rich amorphous poly-alpha olefin.

3. The composition of aspect 2, wherein the 1-butene-rich amorphous poly-alpha olefin comprises a butene-propylene copolymer.

4. The composition of any of aspects 1-3, wherein the 1-butene-based copolymer comprises a semi-crystalline copolymer.

5. The composition of aspect 4, wherein the semi-crystalline copolymer comprises a butene-ethylene copolymer.

6. The composition of any of aspects 1-5, wherein
   the polypropylene homopolymer is present in an amount of between about 20% and about 75% by weight, preferably between about 25% and about 65% by weight, and most preferably between about 30% and about 60% by weight, based on the total weight of the composition;
   the 1-butene-based copolymer is present in an amount of between about 3% and about 50% by weight, preferably between about 4% and about 45% by weight, and most preferably between about 5% and about 35% by weight, based on the total weight of the composition; and
   the plasticizer is present in an amount of between about 20% and about 60% by weight, preferably between about 25% and about 55% by weight, and most preferably between about 30% and about 40% by weight, based on the total weight of the composition.

7. The composition of any of aspects 1-6, wherein:
   the weight average molecular weight of the polypropylene homopolymer is between about 5,000 and about 150,000 daltons, preferably between about 30,000 and about 90,000 daltons, and most preferably between about 35,000 and about 85,000 daltons; and
   the weight average molecular weight of the 1-butene-based copolymer is between about 15,000 and about 160,000 daltons, preferably between about 40,000 and about 150,000 daltons, and most preferably between about 45,000 and about 145,000 daltons.

8. The composition of any of aspects 1-6, wherein:
   the 1-butene-based copolymer comprises a butene-rich amorphous poly-alpha olefin comprising a butene-propylene copolymer;
   the weight average molecular weight of the polypropylene homopolymer is between about 5,000 and about 150,000 daltons, preferably between about 30,000 and about 90,000 daltons, and most preferably between about 35,000 and about 85,000 daltons; and the weight average molecular weight of the butene-rich amorphous poly-alpha olefin is between about 15,000 and about 85,000 daltons, preferably between about 40,000 and about 65,000 daltons, and most preferably between about 45,000 and about 60,000 daltons.

9. The composition of any of aspects 1-8, wherein the weighted average of the weight average molecular weights of the polypropylene homopolymer and the butene-based copolymer is between about 60,000 and about 80,000 daltons, preferably between about 64,000 and about 76,000 daltons, and most preferably between about 66,000 and about 74,000 daltons.

10. The composition of any of aspects 1-9, wherein the viscosity of the composition is equal to or less than about 30,000 centipoise (cP) at 163° C. (325° F.), preferably equal to or less than about 22,500 centipoise (cP) at 163° C. (325° F.), and most preferably equal to or less than about 15,000 centipoise (cP) at 163° C. (325° F.).

11. The composition of any of aspects 1-10, wherein the viscosity of the composition is equal to or less than about 17,500 centipoise (cP) at 177° C. (350° F.), preferably equal to or less than about 15,000 centipoise (cP) at 177° C. (350° F.), and most preferably equal to or less than about 12,500 centipoise (cP) at 177° C. (350° F.).

12. The composition of any of aspects 1-11, wherein heat of fusion of the composition obtained by DSC according to ASTM E793-01 of the composition is less than 40 J/g, preferably less than about 35 J/g, more preferably less than about 25 J/g, more preferably less than about 20 J/g, and most preferably less than about 15 J/g.

13. The composition of any of aspects 1-12, wherein the plasticizer is selected from the group consisting of mineral oil, synthetic poly-alphaolefin oils, and polyisobutylene.

14. The composition of any of aspects 1-13 further comprising an antioxidant.

15. The composition of any of aspects 1-14, wherein the composition does not contain a wax.

16. The composition of any of aspects 1-15, wherein the composition has an elongation at break of at least about 350%, preferably at least about 375%, and most preferably at least about 390%.

17. The composition of any of aspects 1-16, wherein the composition has a stress at yield of at least about 0.5 MPa, preferably at least about 0.7 MPa, and most preferably at least about 0.9 MPa.

18. A method of making a laminate comprising the steps of:
applying the hot melt adhesive composition of any of aspects 1 to 17 in a molten state to a primary substrate; and
mating a secondary substrate to the first substrate by contacting the secondary substrate with the adhesive composition.

19. The method of aspect 18, wherein the first substrate comprises a first layer of an absorbent core and the secondary substrate comprises a second layer of the absorbent core, wherein at least one of the first layer or the second layer have superabsorbent polymers associated therewith.

20. An absorbent core comprising a first layer and a second layer, wherein at least one of the first layer and the second layer comprises superabsorbent polymers, and the first layer and the second layer are adhered to each other by a hot melt adhesive composition of any of aspects 1 to 17 and the superabsorbent polymers form a.

21. A disposable hygiene article comprising the absorbent core of aspect 20.

EXAMPLES

The invention is further illustrated by way of the examples which are set forth below.

To prepare hot melt adhesives, all of the constituents, namely the polymers, the plasticizers, and anti-oxidants, were measured into an aluminum pint can and heated to 177° C. while under a nitrogen blanket (5 scfh). A double-blade impellor in an over-head mixer was lowered into the aluminum can and agitated at 200 rpm until homogenous and at a constant temperature. The formulation is complete when the mix appears homogenous and no clumps from polymer are visible. The formulation can then be used to test viscosity, tensile properties, and/or make laminates to test for end performance.

The ingredients listed below and in Tables 2 and 3 were used to make the adhesives. The values listed in Tables 2 and 3 are for a given raw material in weight percent and should equal to 100%.

CALSOL 5500 is a naphthenic process oil available from Calumet Specialty Products.

Spectrasyn 40 is a liquid poly-alpha-olefin used as a synthetic oil available from ExxonMobil.

INDOPOL H-100 is a polyisobutene oligomer available from Ineos Capital Ltd.

L-MODU S600 is a low modulus, controlled tacticity polypropylene homopolymer available from Idemitsu Kosan Co. Ltd.

L-MODU S901 is a low modulus, controlled tacticity polypropylene homopolymer available from Idemitsu Kosan Co. Ltd.

VESTOPLAST 508 is a butene-rich (1-butene-co-propylene) copolymer available from Evonik Industries.

VESTOPLAST 704 is a propene-rich copolymer available from Evonik Industries

ENGAGE 8137 is an ethylene-octene copolymer available from Dow.

KOATTRO PB M 8911M is a 1-butene copolymer available from LyondellBasell Industries Holdings.

KOATTRO 8510 is a 1-butene copolymer available from LyondellBasell Industries Holdings.

IRGAFOS 168 is a tris(2,4-di-tert-butylphenyl) phosphate available from BASF Chemicals and is used as an antioxidant.

IRGANOX 1010 is pentaerythritoltetrakis(3-(3,5-di-tert-butyl-4-hydroxyphenyl)propionate) available from BASF Corp. and is used as an antioxidant.

TABLE 2

| | EX. 1 | CE. 1 | CE. 2 | EX. 2 |
|---|---|---|---|---|
| CALSOL 5500 | 35.50 | 35.50 | 46.62 | |
| INDOPOL H-100 | | | | 35.50 |
| L-MODU S600 | 46.30 | 46.30 | | 46.30 |
| L-MODU S901 | | | 35.05 | |
| VESTOPLAST 508 | 17.40 | | | 17.40 |
| VESTOPLAST 704 | | 17.40 | | |
| ENGAGE 8137 | | | 17.73 | |
| IRGAFOS 168 | 0.53 | 0.53 | | 0.53 |
| IRGANOX 1010 | 0.27 | 0.27 | 0.60 | 0.27 |
| Viscosity (cP) at 163° C. | 7,475 | 7,500 | 56,000 | 13,550 |
| Elongation at break (%) | 419 | 207 | 431 | 496 |
| Stress at yield (MPa) | 1.31 | 0.96 | 1.01 | 1.27 |

Viscosity was measured according to ASTM D3236 with Spindle 27 at 149, 163, and 177° C. The spindle speed was adjusted so the percent torque was between 45% and 90%. The viscosity was to be low enough to spray or less than about 30,000 cP at 163° C.

Dogbones for tensile tests were made by pouring molten adhesive into silicone molds so that the total dogbone length was 3.5"×1.0" with a thickness, when flush with the mold, of 0.125". The testing area of the dogbone was 0.5"×0.5". A hot spatula was used to scrape away any excess adhesive from the silicone mold so that the thickness of the dogbone was as close to 0.125" as possible. The sample was allowed to cool to room temperature for at least 12 hours before being tested for elongation to break, max stress, and other mechanical tests. The top and bottom of the dogbone were clamped into an Instron tensile tester so that only the 0.5"×0.5" testing area is exposed. The pull rate is 2"/min and continued to pull until the specimens broke. The elongation at break (the "Elongation test") is recorded as a percentage of the based on the difference of final length and the initial length divided by the initial length to determine if the adhesive can withstand the stretch from SAP particles swelling. The goal was to have the adhesive maintain about 400% elongation or greater.

Stress at yield was determined by both the elongation % and stress yield values are automatically calculated in the BlueHill3 Software on the Instron.

Pattern quality was determined qualitatively and quantitatively. The adhesive was heated to approximately 170° C. and pumped through hoses to a Signature Low Flow Nozzle (Nordson Corp.) at 5 gsm coat-weight with a line speed of 200 ft/min. Air-flow was adjusted to create the most visually fiberized-looking pattern with minimal agglomerates (those having a size about more than double the average size of droplet) or fly-away adhesive strands (qualitative). If an adhesive could not produce an acceptable pattern at 170° C., the temperature was increased up to 190° C. Preferably, the application temperature would be below 180° C. On average, air could be anywhere from 10 psi to 40 psi, but this is dependent on the set-up of each piece of equipment and is only intended as a reference, not a rule. The nozzle head was positioned 20 mm above the primary substrate, which was a 33 gsm spunbond nonwoven. The secondary substrate was a release liner so the samples could be better analyzed. Qualitative analysis was done with a microscope to determine the diameter of the fibers produced during the spray application. The goal was to produce fiber diameters less than 60 μm and preferably less than 30 μm. The adhesives tensile properties are a function of the fiber diameter, so the desired fiber diameter may change depending on the adhesive formulation, the desired properties, and other conditions.

The embodiments of the invention shown in Table 2 utilize a 1-butene-based copolymer which is a butene-rich amorphous poly-alpha olefin. Example 1 illustrates one embodiment of the inventive formulation having all necessary components to produce a product with low enough viscosity (desired below about 30,000 cP at 163° C.) and a tensile elongation at break about 400% or greater. Example 1 provided an average fiber diameter of 20 μm when 5 gsm was applied at 170° C. with a Signature Low Flow nozzle available from Nordson. Comparative Example 1 utilizes a propene-rich amorphous poly-α-olefin (APAO) instead of a 1-butene-rich APAO (EX.1); consequently, the elongation at break is too low to be useful, despite maintaining an acceptable viscosity. Comparative Example 2 utilizes an ethylene-octene copolymer instead of the 1-butene-rich APAO of Example 1. Although Comparative Example 2 resulted in an acceptable elongation to break, it had too high of a viscosity at 163° C. to process. Example 2 shows another embodiment of the invention, which utilizes a liquid poly-isobutene as the plasticizing component. Example 2 has a higher, but still suitable, viscosity for processing, further improves the elongation at break.

Alternative embodiments of the inventive formulation utilize a semi-crystalline 1-butene-rich copolymer instead of the 1-butene-rich APAO and are shown as Examples 3-6 in Table 3.

TABLE 3

|  | EX. 3 | EX. 4 | EX. 5 | EX. 6 |
|---|---|---|---|---|
| CALSOL 5500 | 50.20 |  |  |  |
| Spectrasyn 40 |  | 20.00 | 31.12 | 37.28 |
| LMODU S600 |  | 46.43 | 58.08 | 40.21 |
| L-MODU S901 | 29.10 |  |  |  |
| KOATTRO PB M 8911M | 19.90 | 32.77 |  |  |
| KOATTRO 8510 |  |  | 10 | 21.71 |
| Vestoplast 508 |  |  |  |  |
| IRGAFOS 168 | 0.53 | 0.53 | 0.53 | 0.53 |
| IRGANOX 1010 | 0.27 | 0.27 | 0.27 | 0.27 |
| Viscosity (cP) at 325° F. | 12,650 | 30,450 | 19,400 | 16,180 |
| Viscosity (cP) at 350° F. | 9,050 | 21,100 |  |  |
| Elongation at break | 396 | 576 | 584.39 | 420.38 |
| Stress at yield (MPa) | 1.02 | 2.4 | 1.97 | 1.24 |

Examples 3-6 all provided formulations having a suitable elongation at break and good, if not outstanding, stress at yield values. Only the formulation of Example 4 produced an adhesive with a viscosity slightly above the preferred range, but this is still within the scope of the invention. Example 3 produced an average fiber diameter of 22 μm when 5 gsm was applied at 190° C. with a Signature Low Flow nozzle available from Nordson.

Where a range of values is provided, it is understood that each intervening value, and any combination or sub-combination of intervening values, between the upper and lower limit of that range and any other stated or intervening value in that stated range, is encompassed within the range of values recited. In addition, the invention includes a range of a constituent which is the lower limit of a first range and an upper limit of a second range of that constituent.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue or prior invention.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:
1. A hot melt adhesive composition comprising:
   (a) a polypropylene homopolymer having a DSC melting point of less than 100° C.;
   (b) a 1-butene-based copolymer; and
   (c) a plasticizer;
   wherein the composition is tackifier-free.

2. The composition of claim 1, wherein the 1-butene-based copolymer comprises a butene-rich amorphous poly-alpha olefin.

3. The composition of claim 2, wherein the 1-butene-rich amorphous poly-alpha olefin comprises a butene-propylene copolymer.

4. The composition of claim 1, wherein the 1-butene-based copolymer comprises a semi-crystalline copolymer.

5. The composition of claim 4, wherein the semi-crystalline copolymer comprises a butene-ethylene copolymer.

6. The composition of claim 1, wherein the polypropylene homopolymer is present in an amount of between about 20% and about 75% by weight; the 1-butene-based copolymer is present in an amount of between about 3% and about 50% by weight; and the plasticizer is present in an amount of between about 20% and about 60% by weight.

7. The composition of claim 1, wherein:
the weight average molecular weight of the polypropylene homopolymer is between about 5,000 and about 150,000 daltons; and
the weight average molecular weight of the 1-butene-based copolymer is between about 15,000 and about 160,000 daltons.

8. The composition of claim 1, wherein:
the 1-butene-based copolymer comprises a butene-rich amorphous poly-alpha olefin comprising a butene-propylene copolymer;
the weight average molecular weight of the polypropylene homopolymer is between about 5,000 and about 150,000 daltons; and
the weight average molecular weight of the butene-rich amorphous poly-alpha olefin is between about 15,000 and about 85,000 daltons.

9. The composition of claim 1, wherein the weighted average of the weight average molecular weights of the polypropylene homopolymer and the butene-based copolymer is between about 60,000 and about 80,000 daltons.

10. The composition of claim 1, wherein the viscosity of the composition is equal to or less than about 30,000 centipoise (cP) at 163° C. (325° F.), preferably equal to or less than about 22,500 centipoise (cP) at 163° C. (325° F.), and most preferably equal to or less than about 15,000 centipoise (cP) at 163° C. (325° F.).

11. The composition of claim 1, wherein the viscosity of the composition is equal to or less than about 17,500 centipoise (cP) at 177° C. (350° F.).

12. The composition of claim 1, wherein heat of fusion of the composition obtained by DSC according to ASTM E793-01 of the composition is less than 40 J/g.

13. The composition of claim 1, wherein the plasticizer is selected from the group consisting of mineral oil, synthetic poly-alphaolefin oils, and polyisobutylene.

14. The composition of claim 1 further comprising an antioxidant.

15. The composition of claim 1, wherein the composition does not contain a wax.

16. The composition of claim 1, wherein the composition has an elongation at break of at least about 350%.

17. The composition of claim 1, wherein the composition has a stress at yield of at least about 0.5 MPa.

18. A method of making a laminate comprising the steps of:
applying the hot melt adhesive composition of claim 1 in a molten state to a primary substrate; and
mating a secondary substrate to the first substrate by contacting the secondary substrate with the adhesive composition.

19. The method of claim 18, wherein the first substrate comprises a first layer of an absorbent core and the secondary substrate comprises a second layer of the absorbent core, wherein at least one of the first layer or the second layer have superabsorbent polymers associated therewith.

20. An absorbent core comprising a top layer and a bottom layer, wherein at least one of the top layer and the bottom layer comprises superabsorbent polymers, and the top layer and the bottom layer are adhered to each other by a hot melt adhesive composition of claim 1 and the adhesive composition adheres the superabsorbent polymers within the absorbent core.

21. A disposable hygiene article comprising the absorbent core of claim 20.

* * * * *